United States Patent [19]

Lewis et al.

[11] Patent Number: 5,288,288
[45] Date of Patent: Feb. 22, 1994

[54] METHOD AND A DEVICE FOR COLD LASER MICROSURGERY WITH HIGHLY LOCALIZED TISSUE REMOVAL

[76] Inventors: Aaron Lewis; Daniel Palanker, both of Neve Shanan, 18/14 Jerusalem, Israel

[21] Appl. No.: 778,736

[22] Filed: Oct. 22, 1991

[30] Foreign Application Priority Data

Oct. 23, 1990 [IL] Israel .................................... 096092

[51] Int. Cl.$^5$ ............................................ A61B 17/36
[52] U.S. Cl. .......................................... 606/14; 606/2; 606/17; 606/28
[58] Field of Search ............... 604/43, 45, 173; 606/2, 606/3, 4, 9, 10, 13–16, 28; 128/772, 395; 385/147

[56] References Cited

U.S. PATENT DOCUMENTS

| | | |
|---|---|---|
| 4,659,429 | 4/1987 | Isaacson et al. . |
| 4,880,496 | 11/1989 | Nebenzahl et al. . |
| 4,917,462 | 4/1990 | Lewis et al. . |
| 5,123,902 | 6/1992 | Müller et al. .......................... 604/43 |

OTHER PUBLICATIONS

"Development of A 500 A Spatial Resolution Light Microscope" A. Lewis, M. Isaacson, A. Harootunian and A. Muray *Ultramicroscopy* 13 (1984) 227–232.
"Super-resolution Fluorescence Near-field Scanning Optical Microscopy" A. Harootunian, E. Betzig, M. Isaacson and A. Lewis Appl. Phys. Lett. 49 (11), Sep. 15, 1986 pp. 674–676.
"New Form of Scanning Optical Microscopy", R. C. Reddick, R. J. Warmack, and T. L. Ferrell *Physical Review B* vol. 39, No. 1, Jan. 1, 1989 pp. 767–770.
"Optical Stethoscopy: Image Recording with Resolution" λ/20 D. W. Pohl, W. Denk, and M. Lanz Appl. Phys. Lett. 44 (7), Apr. 1, 1984 pp. 651–653.
"Near-field Optical-scanning Microscopy", U. Durig, D. W. Pohl, and F. Rohner J. Appl. Phys. 59 (10), May 15, 1986, pp. 3318–3327.
"Optical Characteristics of 0.1 μm Circular Apertures in a Metal Film as Light Sources for Scanning Ultramicroscopy" J. Vac. Sci. Technol. B 3(1), Jan./Feb. 1985 pp. 386–389.
"Development of High-Resolution Optical Scanning Fluorescence Microscopy" Satoshi Okazaki et al. *Mikrochimica Acta* [Wien] 1988, III, 87–95.
"Scanning Tunneling Optical Microscopy" D. Courjon, K. Sarayeddine and M. Spajer, Optics Communication vol. 71, No. 1,2 May 1, 1989.
"A Light Source Smaller Than the Optical Wavelength", K. Lieberman, S. Harush, A. Lewis, and R. Kopelman *Science*, Jan. 5, 1989, vol. 247, pp. 59–61.
"Cold Laser Microsurgery of the Retina with a Syringe Guided 193 nm Excimer Laser" Proceedings of Ophthalmic Technologies, SPIE vol. 1423 (1991) pp. 98–102.
"Technique for Cellular Microsurgery Using the 193-nm Excimer Laser" Lasers in Surgery and Medicine 11:580–586 (1991) pp. 580–586.
"Ultraviolet Laser Ablation of Organic Polymers" Chem. Rev. 1989, 89, 1303–1316.

*Primary Examiner*—Stephen C. Pellegrino
*Assistant Examiner*—Jeffrey A. Schmidt
*Attorney, Agent, or Firm*—Jones, Tullar & Cooper

[57] ABSTRACT

A method and apparatus for highly localized treatment of biological tissue by a laser includes a micropipette having a tip with a central opening having a diameter of less than about 10 microns. The micropipette is mounted on an articulated arm for precision motion with respect to tissue to be treated. Gas is supplied to the micropipette to prevent the entry of liquid, and laser light supplied through the articulated arm is directed into the pipette. The pipette is positioned in X, Y and Z directions with respect to the tissue to control the location and depth of treatment.

A protective window may be positioned at the tip of the micropipette to prevent the entry of liquid.

21 Claims, 3 Drawing Sheets

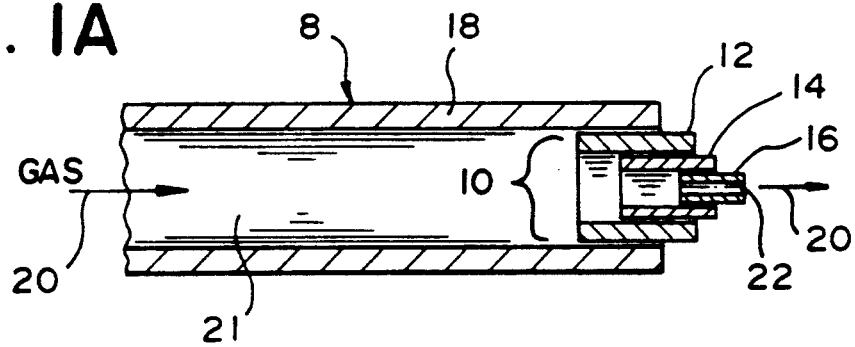
FIG. IA
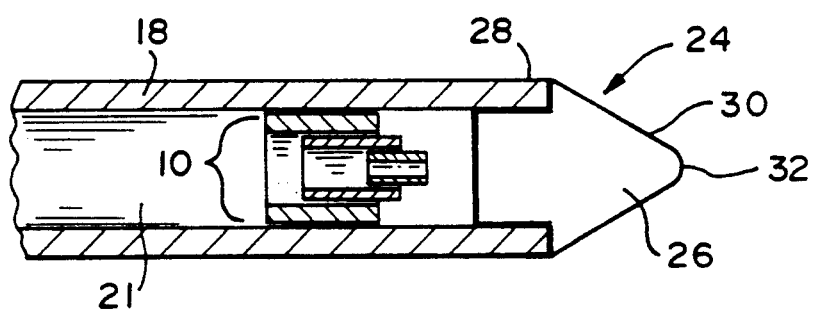
FIG. IB
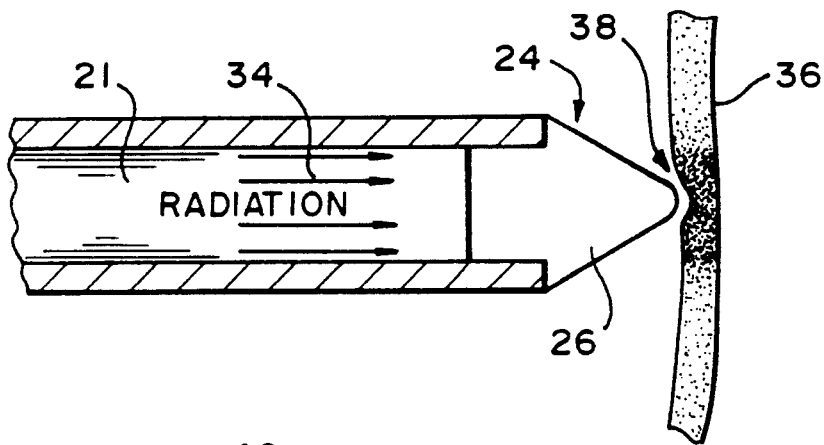
FIG. IC
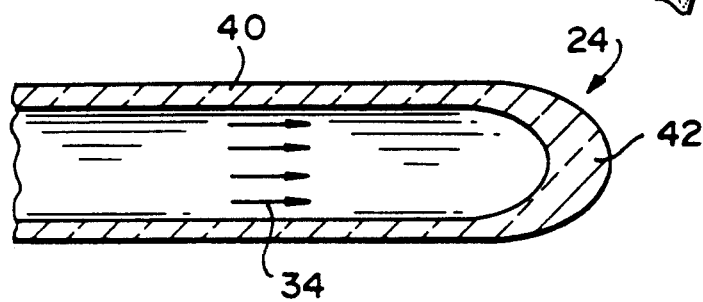
FIG. ID

METHOD AND A DEVICE FOR COLD LASER MICROSURGERY WITH HIGHLY LOCALIZED TISSUE REMOVAL

FIELD OF THE INVENTION

The invention is directed, in general, to cold laser microsurgery, and more particularly to a method and a device for high precision tissue removal without causing physiological damage to the surrounding tissue. The accuracy of the device can be less than a micron in the XY plane and 0.1 micron in the Z direction.

BACKGROUND OF THE INVENTION

The laser has been applied in surgical procedures for many years. However, in all of these applications the lack of highly precise methods or devices often resulted in damage to the encircling cells. In many applications the effect of the laser in a wide variety of wavelength regimes is due to the production of heat; however, this heat is hard to confine, so that often the zone of thermal damage is considerably larger than the actual laser spot interacting with the tissue. In other applications, tissue removal is caused by dielectric breakdown in the tissue, caused by a highly focused laser beam in a wavelength regime that is normally associated with thermal effects only. This dielectric breakdown can be carried out with high Z resolution only under stringent optical conditions that require high numerical aperture lenses with a short focal length. These conditions restrict the use of this method to regions of the body that would allow the introduction of a lens close (a few millimeters) to the surgical surface. Furthermore, this type of laser/tissue interaction also produces damaging shock waves.

In order to provide laser microsurgery that is highly precise, a laser is required that can have a variable spot size from dimensions of a few microns and which has Z-direction resolution of at least a micron. Such a laser would produce no thermal or other spatially hard to confine damage to the surrounding tissue in all three dimensions.

To meet these requirements, it would be ideal for a laser to interact with biological tissue in a photochemical rather than a thermal mode. Biological tissue is composed of molecules that are principally formed of carbon, nitrogen and oxygen. The bonds that these atoms make have energies of dissociation in a regime that corresponds to the deep ultraviolet region of the electromagnetic spectrum. There is a laser, known as argon fluoride (ArF) excimer laser, which operates at 193 nm, and which is the shortest wavelength laser that can propagate in air. It has been shown [R. Srinivasan and B. Braren, Chem. Rev. 89, 1303 (1989)] that such a laser wavelength is absorbed by biopolymeric molecules which are then raised by the radiation to a dissociative excited state. Once in such an excited state, the molecules enter a photochemical pathway in which there is direct break-up of the molecular bonds. In principle, all of the energy of the photon in the foregoing ablation process goes to break up the molecules rather than heat the material. In fact, however, excimer lasers exhibit many emissions some at longer and others at shorter wavelengths. The longer wavelengths at 248 nm and 308 nm result in ablation but with increasing thermal effects and depth of penetration. In addition these wavelengths are known to cause damage to genetic material. Available laser wavelengths shorter than 193 nm can only propagate in vacuum, but of greater importance is the fact that 193 nm is the shortest wavelength for which optical elements exist to guide and focus the beam, and such elements function in a fashion that is considerably less precise than that required for the microsurgery applications envisioned by the present invention. Specifically, lenses in this region exhibit considerable aberration, thus making their focal point too big for microsurgery. In addition to these optical limitations, there is a further problem in the use of the ArF excimer laser within biological aqueous solutions; namely, that such solutions cause a strong absorption of the 193 nm radiation. This limits the penetration of the radiation in the solution to a few microns. The instrument disclosed herein overcomes all of these problems and allows for microsurgery with unparalleled precision in the X, Y and Z direction without heat damage to the surrounding tissue.

The principal application of the ArF excimer laser in medicine is in the field of refractive surgery. In this area there are two approaches, both of which have to work within the boundaries of the limitations discussed above. The application of refractive surgery uses the lack of heating of the surrounding tissue to remove layers of the cornea with the aid of a slit that produces a line image of the laser or with the aid of a variable aperture that allows the form of the corneal refraction to be changed. Actually, this application is not microsurgery and in fact there is presently no microsurgery performed with the ArF excimer laser. Furthermore, such applications do not encounter the problem of ablating tissue in a surrounding liquid which is encountered in the majority of microsurgical operations.

SUMMARY OF THE INVENTION

A device and a method is disclosed for focusing an ArF excimer laser in the XY plane, using tapered tubes made of materials such as metal or glass. The tubes are connected to an articulated arm that allows freedom of aiming the laser in any direction. Gas pressure, flow and/or microwindows give the device the ability to work in and on biological solutions. The device also includes a variety of other laser beams that can be colinearly focused with the ArF laser. This permits a series of parallel operations to be performed, such as, for example, resealing of blood vessels cut by the excimer laser.

DESCRIPTION OF THE FIGURES

The foregoing, and additional objects, features and advantages of the present invention will be understood from the following detailed description of a preferred embodiment thereof, taken in conjunction with the accompanying drawings, in which:

FIGS. 1A-1D are diagrammatic representations of tapered tubes for focusing a laser in accordance with the present invention;

DESCRIPTION OF THE INVENTION

Figure 2:
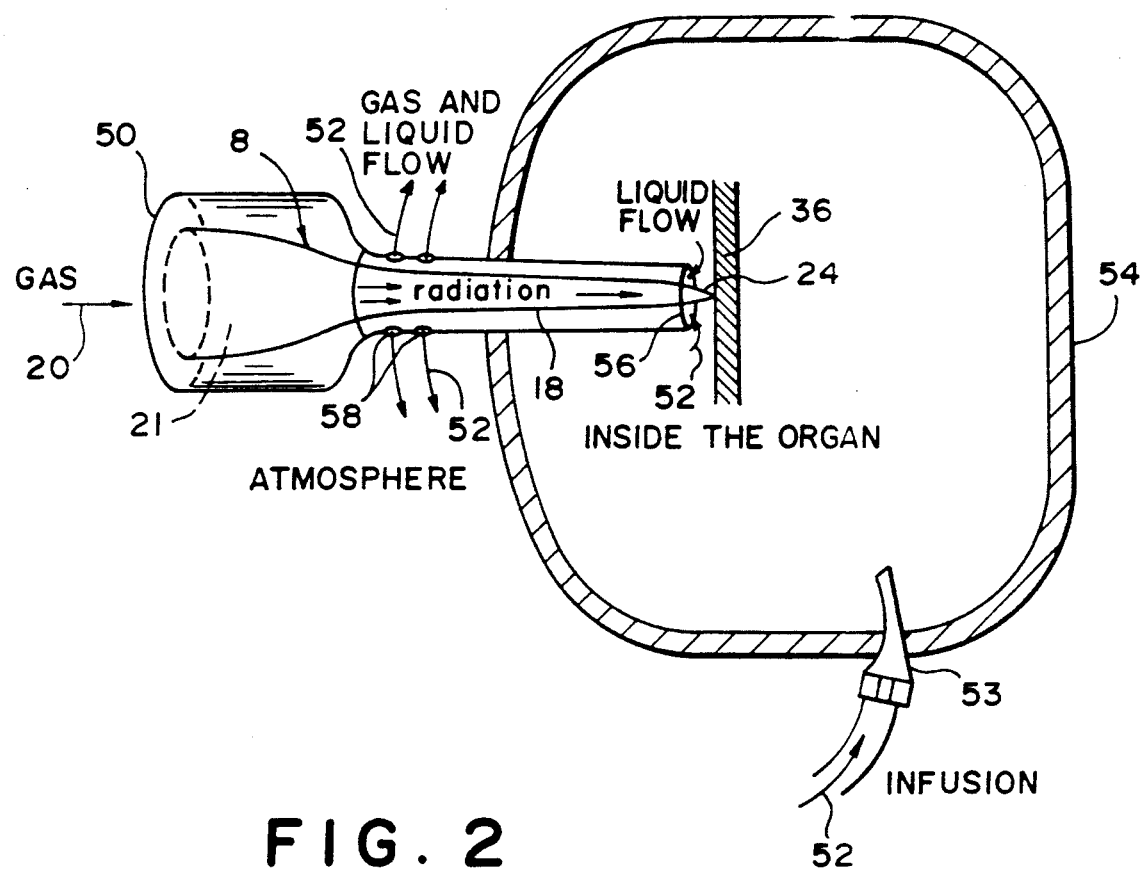
FIG. 2 is a diagrammatic representation of the use of the tapered tube of FIG. 1, without windows and in a liquid environment.

The essential methodology of the focusing device of the present invention has two crucial features; first, a tapered tube to guide and aperture the excimer laser radiation, and second means for preventing liquid from entering the tube. The availability of a tapered guide tube is not enough for the microsurgery applications envisioned because of the fact that as soon as such a tube is inserted into the aqueous environment of a biological structure it would fill up with liquid, and this would prevent the transmission of the excimer laser to the point of interest. Therefore, it is a second essential feature of the invention that there be a means for preventing liquid from entering into such tubes.

In one application of the present device to microsurgery, tapered glass pipettes are prepared by the established procedure of pulling glass microcapillaries, as is used in a variety of areas in biology. However, such a tapered pipette will not work for guiding and aperturing an excimer laser in liquids because of the reasons mentioned above. To overcome this problem a static gas pressure is introduced into the tube which is equal to the capillary force that the pipette exerts. This frees the tube from the problems caused by working in liquids and permits this embodiment of the device to be used in cell surgery when appropriate micromanipulators are attached to the tapered pipette to allow it to approach the surface of the cell. The working distances in such an application are very small because of the absorption of laser light by the surrounding liquid. Thus, the tapered end of the glass pipette needs to be brought within a micron or less of the surface to be irradiated. Because of this absorption, any radiation that may leak out through the glass of the pipette is prevented from causing any deleterious effects by the liquid that surrounds the pipette. When smaller diameter pipettes are used, higher pressure is needed to prevent liquid entering. However, under this pressure it is hard to prevent pipette breakage during the laser ablation process.

Another possibility for solving the problem of liquid entering into the pipette is available. The pipette can either be made or coated with hydrophobic material. This approach would allow one to reach even higher XY resolutions of surgical alternations up to ~0.1 micron.

Even though the foregoing approach to tapered tubes is excellent for cell surgery with dimensions where the tapered tip is below 10 microns, the technique is not usable for tissue microsurgery for several reasons. First, the glass pipette may break within the organ. Even if the surgeon does not accidentally break the pipette, the glass can be broken because of mechanical forces and ablation of the walls induced by the higher intensity of the transmitted laser beam necessary for tissue microsurgery. Second, for tissue rather than cellular microsurgery, the tip dimension is generally large (>10 microns). For such dimensions the method of static gas pressure is not effective in preventing at the same time the liquid from entering the pipette. Furthermore, the formation of gas bubbles which exit the tube may visually obscure the tissue that is being ablated by the 193 nm radiation.

The tapered tube illustrated generally at 8 in FIG. 1A overcomes the problems in tissue microsurgery stated above. In this instrument a series 10 of telescoped short tubes 12, 14 and 16 with increasingly smaller diameters are inserted into one end of a tubular needle 18 such that the last protruding tube 16 is of the diameter required for the surgical application at hand. In the case of wet tissue that needs to be ablated, where the tissue is in an air surrounding, i.e., in ambient air, there is a problem with the thin liquid layer that covers the tissue, particularly if the liquid absorbs at 193 nm radiation. This problem is overcome by using the tapered tube 8 and by applying a gas flow, indicated by arrow 20, through the central, axially extending opening 21 of the needle 18. The gas exits the tip 22 of the tube, and produces a small dry region adjacent the tip, with a diameter equal to the diameter of the tip. This occurs as a result of the gas flow pushing out the liquid layer in the place that the gas is applied to the tissue.

For working in a liquid surrounding; i.e., in ambient liquid, it's necessary to prevent the entry of the liquid into the tube. For that purpose, a window 24 formed from a material 26 transparent to the 193 nm deep ultraviolet light is inserted in or around the end 28 of the needle 18 (see FIG. 1B). In the case of a highly absorbing liquid surrounding the tissue, the window has a tapered, cone-shaped forward surface 30 which works like an aperture because the ablation occurs only in that region of the tissue where the energy fluence is enough for ablation, and this is possible only in close proximity (a few microns) to the tip 32 (see FIG. 1C) of the window material 26. In this case the series 10 of tubes can be moved back in the needle 18, or removed entirely from the needle, as shown in FIGS. 1B and 1C, respectively. The tip 32 of window material 26 serves to concentrate the light, indicated by arrows 34, onto a biological tissue 36 to produce an ablated region 38. If instead of the needle 18 a fused silica pipette 40 is used, (see FIG. 1D) the window 24 may be formed by closing the end 42 of the pipette by heating to prevent the entry of liquid. The light 34 passes through the end 42, and this end can be placed in close proximity to the tissues being treated.

Alternatively, the addition of a tube that is concentric to the tapered needle allows the use of the gas flow method even in a liquid surrounding. This overcomes the need for a window at the end of the needle. As illustrated in FIG. 2, this method of preventing liquid from entering the central needle 18, which may be the needle of FIG. 1A, utilizes a gas 20 which is passed through the central opening 21 and returns through an outer concentric needle 50 which extends over needle 18. A liquid flow is generated by a liquid 52 that is continually being infused through an inlet 53 into the tissue or organ 54 being treated. This liquid flows through the annular opening 56 formed by the inner and outer tubes 18 and 50 and out through holes 58 in the side of the outer needle (see FIG. 2) outside the organ 54. This liquid flow is natural in many surgical procedures and entrains the gas 20 exiting the tip 22 to prevent the escape of bubbles into the medium surrounding the tissue being treated. This also helps to evacuate a small amount of gas microbubbles and liquid products of ablation of the tissue.

Figure 3:
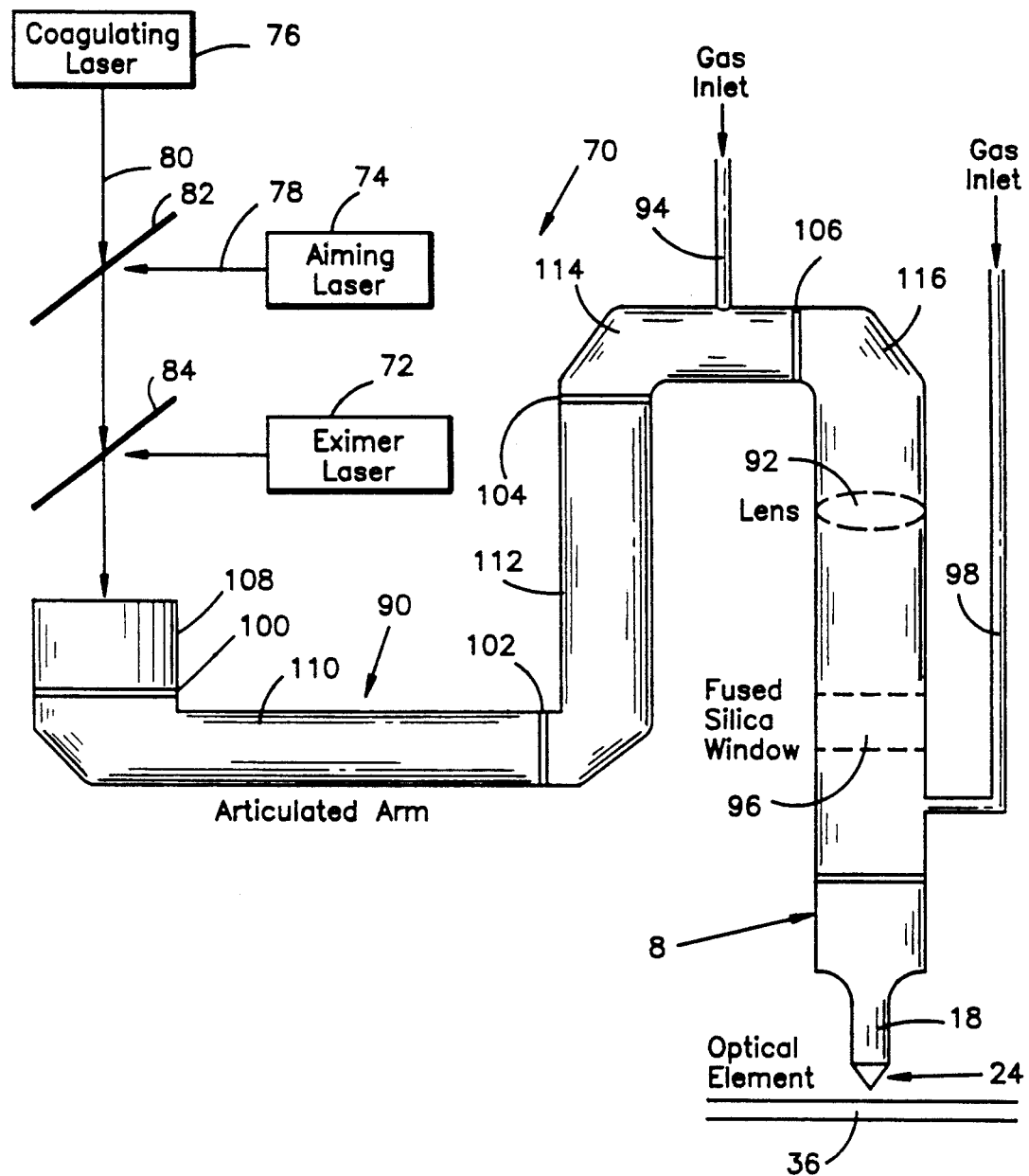
FIG. 3 is a diagrammatic illustration of an articulated area supporting the tapered tube of FIGS. 1 and 2.

A device for use in microsurgery and similar applications is illustrated diagrammatically at 70 in FIG. 3, and utilizes several lasers. In addition to an excimer laser 72, aiming and coagulating lasers 74 and 76 are provided. The lasers 74 and 76 provide aiming and coagulating beams 78 and 80 that may be required to operate at the same time as the excimer laser or at some time before or after the excimer laser. In addition to these lasers and their associated guiding optical elements, which can be mirrors 82 and 84 that are selective to the particular frequencies of the lasers being used, there is an articulated arm 90 which serves as an optical waveguide and this has appropriate optical elements such as mirrors (not shown) and lenses such as lens 92 to guide the excimer and the other laser beams to the optical element 8, which is the tapered tube of the present invention. In order to overcome the problem of absorption of the 193 nm radiation by air inside the articulated 90, a gas inlet 94 is provided, through which the articulated arm is filled with Nitrogen or other gas that doesn't absorb this radiation.

The interior of the articulated arm 90 is separated from the interior of the optical element 8 by a fused silica window 96, which allows light from the lasers 72, 74, and 76 to pass into the interior of element 8. A second gas inlet 98 is also provided to supply gas to the optical element 8 which is secured to the articulated arm and which moves with the arm with respect to tissue 36. The optical element 8 can be the element shown in any of FIGS. 1A–1D, and preferably takes the form of the device illustrated in FIG. 2.

The articulated arm 90 includes plural joints, generally indicated at 100, 102, 104 and 106 which permit adjustment of the arm elements 108 110, 112, 114 and 116 to position the optical element 8. The motion of the articulated arm is controlled in any known manner to provide precise control of the location of needle 18 and the tip 16, together with its covering window 24 in cases where the window is required.

Numerous applications are possible for microsurgery in cells and tissues, such as making perforations of outer layers in cells, cell membranes or cell walls and such layers as the zona pellucida of oocytes for in vitro fertilization. In addition, the technique of the invention can be used in biological and medical studies where specific parts of cells and occytes or connections between cells need to be cut without damage to the surrounding tissue. This can also include cleaning of cell surfaces without damage to underlying layers. Such removal of biological material without affecting underlying layers is also applicable to a wide variety of tissue removal procedures including removal of scar tissue from brain slices or removal of membranes from the retina that obscure light from reaching the photoreceptors. Furthermore the microsurgical capabilities of our device can be used with facility in neurosurgery, in eye surgery such as the conjunctiva, in the removal of fungi etc., in the removal of materials from the spinal column, in dermatological procedures that require fine regulation of material removal in X, Y and/or Z directions, in the fine cutting required in plastic surgery, in small organ donation etc., in selective removal of soft tissue from hard tissue such as in cavities in teeth, or other cleaning and sterilization procedures in teeth.

Several experiments were completed to demonstrate the effectiveness of the foregoing. First, in the field of cell surgery the fine production of holes in the zona pellucida of oocytes without damage for in vitro fertilization procedures has been demonstrated. Second, the selective removal without heating of soft tissue from teeth including that which is found in cavities, has been demonstrated. Third, the accurate removal of layers of tissue from the retina and the conjunctiva with very fine X, Y and Z control has been demonstrated.

Thus, there has been disclosed a unique structure and method for use in microsurgery. The structure as described above thus comprises a micropipette formed of glass, metal, or other suitable material and including a tip having a central opening of less than 10 microns. The pipette tip can be formed by drawing a glass tube, or can be formed by a set of telescoping tubes wherein the diameter of the innermost tube has the desired dimension. The pipette is mounted on a delivery device such as an articulated arm which is movable to position the tip of the pipette in X, Y and Z directions with respect to a material to be treated. The tip can be open, in which case a gas under pressure may be supplied to the pipette to keep liquid out, or the tip can be closed by a window material which can fit over the tip or be inserted into it, in order to prevent absorption of the laser light supplied through the pipette. If the material being treated is in air, with a wet surface, the open tip is preferred, since the flowing gas can blow the moisture away from the location to be treated by the laser. However, if material is immersed in liquid, a closed tip is preferred. If desired, however, an open tip can be used when the material to be treated is immersed. In this case, a gas is supplied to keep the liquid out of the pipette, and it is preferred that a concentric tube be placed around the pipette to evacuate bubbles formed in the liquid. Although the invention has been described in terms of preferred embodiments, it will be understood that variations may be made without departing from the true spirit thereof, as set out in the following claims.

What is claimed is:

1. Apparatus for directing laser light to a material to be treated, comprising:
    a micropipette having an axially extending interior opening terminating in a tip having an interior diameter of about 10 microns;
    delivering means adjustably supporting said micropipette for motion with respect to the material being treated,
    means supplying laser radiation to said micropipette for delivery through said tip to the material being treated, said laser radiation being delivered to said material with a resolution of less than about 10 microns; and
    means preventing the entry of liquid into said micropipette tip from the region of the material being treated, whereby said laser light passes through said pipette without absorption by such liquid.

2. The apparatus of claim 1, wherein said micropipette tip includes a set of telescoping tubes located at a terminal end of said micropipette, an outermost tube of said set being received within said terminal end of said micropipette and the inner diameter of an innermost tube of said set having a diameter less than 10 microns.

3. The apparatus of claim 2, wherein said means preventing the entry of liquid comprises a source of gas under pressure, and means supplying said gas under pressure to the interior of said micropipette.

4. The apparatus of claim 2, wherein said means preventing the entry of liquid comprises window means.

5. The apparatus of claim 4, wherein said window means is transparent to said laser light.

6. The apparatus of claim 5, wherein said window means closes said terminal end of said micropipette.

7. The apparatus of claim 2, wherein said innermost tube extends out of the terminal end of said micropipette and forms the tip thereof.

8. The apparatus of claim 2, wherein said set of telescoping tubes is located within the terminal end of said micropipette, said means preventing the entry of liquid comprising a window closing said terminal end of said micropipette.

9. The apparatus of claim 8, wherein said window is transparent to said laser radiation and includes a tapered, cone-shaped forward surface for concentrating said radiation onto said material to be treated.

10. The apparatus of claim 1, wherein said means preventing the entry of liquid into said micropipette tip comprises a source of gas under pressure.

11. The apparatus of claim 1, wherein said means preventing the entry of liquid into said micropipette tip comprises window means transparent to said laser light.

12. The apparatus of claim 1, wherein said means preventing the entry of liquid into said micropipette comprises:
   a source of gas under pressure;
   means supplying said gas to said tip, said gas flowing out of said tip in the region of said material to be treated;
   means surrounding said micropipette and defining a passage therebetween, and
   means entraining said gas flowing out of said tip and carrying said entrained gas through said passage to evacuate said gas.

13. The apparatus of claim 1, wherein said laser radiation is radiation in the deep ultraviolet for ablation of material in biological media.

14. The apparatus of claim 1, wherein said means preventing entry of liquid into said micropipette tip includes a window closing the terminal end of said micropipette, said window being transparent to said laser radiation and including a tapered, cone-shaped forward surface for concentrating said radiation onto a material to be treated.

15. The apparatus of claim 1, wherein said micropipette is fused silica, and wherein the terminal end of said micropipette is closed by said silica.

16. The apparatus of claim 1, further including an outer tube concentric with and surrounding said micropipette for establishing a fluid flow which prevents the entry of liquid into said micropipette.

17. The apparatus of claim 16, wherein said delivering means includes movable arm means supporting said micropipette and incorporating means directing said laser radiation to said micropipette.

18. A method of microsurgical treatment of biological media, comprising:
   producing laser radiation in the deep ultraviolet wavelength;
   confining said radiation by directing it through a tapered micropipette having an exit tip having a diameter of less than 10 microns and having means for preventing the entry of liquid into said micropipette tip; and
   positioning said micropipette to locate said exit tip adjacent a region of interaction in media to be treated, thereby to direct said laser radiation onto the media in order to remove tissue from said media, said tapered micropipette confining said laser so that the region of interaction of said laser with said media is confined to dimensions on the order of 10 microns.

19. The method of claim 18, further including supplying gas under pressure to said micropipette to produce a gas flow through said exit tip and to permit the removal of tissue in the presence of liquid.

20. The method of claim 18, further including entraining gas flowing from said exit tip and removing entrained gas from said region of interaction.

21. The method of claim 20, further including mounting said micropipette on a delivery system for mechanically positioning said exit tip.

* * * * *